(12) United States Patent  (10) Patent No.: US 7,634,122 B2
Bertram et al.  (45) Date of Patent: Dec. 15, 2009

(54) REGISTERING INTRAOPERATIVE SCANS

(75) Inventors: Michael Bertram, Markt Schwaben (DE); Robert Essenreiter, München (DE)

(73) Assignee: BrainLAB AG, Feldkirchen (DE)

( * ) Notice: Subject to any disclaimer, the term of this patent is extended or adjusted under 35 U.S.C. 154(b) by 706 days.

(21) Appl. No.: 11/211,170

(22) Filed: Aug. 24, 2005

(65) Prior Publication Data

US 2006/0050942 A1  Mar. 9, 2006

Related U.S. Application Data

(60) Provisional application No. 60/609,164, filed on Sep. 10, 2004.

(30) Foreign Application Priority Data

Aug. 25, 2004 (EP) .................................. 04020197

(51) Int. Cl.
*G06K 9/00* (2006.01)
(52) U.S. Cl. ...................................... 382/128; 128/922
(58) Field of Classification Search ................ 382/128, 382/129–132; 128/922
See application file for complete search history.

(56) References Cited

U.S. PATENT DOCUMENTS 6,678,545 B2  1/2004  Bucholz
7,359,746 B2 *  4/2008  Arata .......................... 600/424
2002/0065461 A1 *  5/2002  Cosman ....................... 600/426
2004/0127788 A1 *  7/2004  Arata .......................... 600/424

FOREIGN PATENT DOCUMENTS

| EP | 1 378 206 A1 | 1/2004 |
| WO | 01/01845 A2 | 1/2001 |
| WO | 01/87136 A2 | 11/2001 |
| WO | 2004/023103 | 3/2004 |

OTHER PUBLICATIONS

European Search Report for corresponding Application No. 04020197.2 dated Feb. 4, 2005.
European Office Action for Application No. 04 020 197.2 dated Feb. 15, 2008.

* cited by examiner

*Primary Examiner*—Aaron W Carter
(74) *Attorney, Agent, or Firm*—Renner, Otto, Boisselle & Sklar LLP

(57) ABSTRACT

A system and apparatus for registering image data of a body, wherein the image data are captured in a detection range and the body is subsequently shifted relative to the detection range or vice versa. The image data are registered from the detected position of a first marker array, arranged in a defined positional relationship relative to the body, and from the detected position of a second marker array, arranged in a defined positional relationship relative to the detection range. The apparatus includes a camera and a first marker array that is arranged in a known positional relationship relative to the body, wherein a second marker array is arranged at a fixed position relative to a detection range.

18 Claims, 2 Drawing Sheets

REGISTERING INTRAOPERATIVE SCANS

RELATED APPLICATION DATA

This application claims priority of U.S. Provisional Application No. 60/609,164 filed on Sep. 10, 2004, which is incorporated herein by reference in its entirety.

FIELD OF THE INVENTION

The invention relates to a device and method for automatically registering image data, in particular intra-operative CT scans for use in a navigation method, in order to detect the effects of changes in a body following surgery.

BACKGROUND OF THE INVENTION

If the internal structure of a body is changed by surgery, for example in a pelvic or brain operation, either by the surgery itself (e.g., advancing a guiding wire) or by after-effects (e.g., organs or tissue sagging), then it often can be useful if image data of the body are captured intra-operatively in order to detect the changes caused by the surgery. As used herein, the term "intra-operatively" refers to a period after a surgery and a period prior to further surgery.

Thus, for example, in a pelvic operation it is possible to check by one or more intra-operative scans the position at which a drill is situated in a bone. To this end, for example, a patient with a marker attached to him/her can be inserted into a computer tomograph. Computer tomography is performed on the patient and the patient is removed from the computer tomograph in order to perform further surgery. In such circumstances, it is advantageous if the patient is immobilized, e.g., the patient is situated in a fixed position relative to a table.

U.S. Pat. No. 6,678,545 B2 discloses a prior art system for use in imaging a subject and determining a position relative to a body of a patient. More particularly, this system can be used to determine a position of a probe within a head and display an image corresponding to the determined position. A drawback to this system, however, is that the probe and patient must be scanned together. The probe must be fully visible in the three-dimensional data set and, thus, can be an obstacle. Further, the probe may cause artifacts, which can deteriorate the image quality.

SUMMARY OF THE INVENTION

Image data of a body can be captured in a detection range, for example in a nuclear spin tomograph or computer tomograph. It is not necessary during the detection process for a reference star or other markers to be present on the body of the patient or near the patient, e.g., on a table on which the patient is lying. The image data can be captured in a variety of ways known from the prior art. For example, the body or the table can be moved through the detection range during the recording process, advancing constantly and continuously as in spiral computer tomography. Alternatively, the body or table can be advanced in increments, and a recording can be taken each time the table has been advanced by a particular length, with the table in a motionless, fixed position during recording.

The body or table can be incremented until they leave the detection range or until the desired area has been recorded. On the other hand, the detection device, e.g., the detection range along the body, also can be moved in order to record the body or parts of the body in increments. The detection device also can be constantly advanced, for example, by moving a data capture device on rails parallel to the body or table and fixing the table and/or body.

Irrespective of whether the body and/or the detection device is moved, it is possible to allude to a movement of the body relative to the detection range. The body or the table thus can be shifted relative to the detection range or vice versa.

Once the image data have been captured, the body can be shifted out of the detection range, e.g., out of the nuclear spin tomograph, or the detection range can be shifted relative to the body, wherein markers such as, for example, a first marker array including three, four or more markers, or a reference star, can be attached to the patient or to the table on which the patient is supported. Preferably, the patient and/or markers/reference star can be fixed such that they do not move with respect to one another. This fixed relationship between the patient and/or the markers can be implemented once the body of the patient has been shifted, e.g., once a table on which the patient is supported is extended or moved from the detection range.

If markers, such as a second marker array having three, four or more markers or also a reference star, are attached to a defined position relative to the detection range, e.g., to the detection device such as the computer tomograph itself, then the body once removed from the detection range can be registered if the advancing direction, distance and a possible rotation of the body are known, e.g., if the distance and direction the body has been removed from the detection range is detected or otherwise known.

Initially, the body in the detection range can be registered and, for example, can be navigated by the second marker array, which, as noted above, can be arranged in a defined positional relationship to the detection range, e.g., on the scanner itself, wherein said positional relationship can be determined by a first transformation or registration method. This first transformation or registration method need not be re-executed unless the marker or markers arranged relative to the detection range are offset, e.g., attached or moved to another point on the detection device. Thus, after recording in the detection range, the body of the patient can be registered provided the markers and/or the second marker array have not been moved relative to the detection range.

Since the body or the table can be moved out of the detection range for further surgery, the first marker array can be attached to the body itself or in a fixed relative positional relationship to the body, such as to the table, once the body or table has been moved out of the detection range. The exact position or the distance of the first marker array relative to the body need not be known; however, the first marker array can be arranged fixed or otherwise immobile, such that it has a constant distance or a fixed positional relationship or a fixed position relative to the body, which preferably is supported in a fixed or non-movable manner. The body then can be registered if the positional relationship between the first and the second marker array is known, which is designated as a second transformation method.

To this end, information regarding spatially shifting the body out of the detection range can be used as a third transformation method. If the positional relationship of the second marker array relative to the detection range (i.e., the first transformation) and the translation or shift of the body out of the detection range (i.e., the third transformation) are known, then the body can be registered. The second transformation (i.e., the positional relationship of the first marker array to the second marker array) then can be ascertained, which allows navigation of the body using the first marker array.

The first marker array can also be attached to the body and/or the table on which the patient is supported, preferably in a fixed manner, by a reference star adaptor, as described in EP 04 003 019 belonging to the Applicant, wherein the teaching of EP 04 003 019 regarding the embodiment of a reference star adaptor is incorporated into this application. Such a reference star adaptor enables a reference star attached to a body or instrument, such as the table, to be automatically or manually repositioned. For example, the reference star can be rotated about one or more joints and/or shifted along one or more predetermined directions, wherein at least one position detector, which is connected to a mounting between the reference star and the reference adaptor, can ascertain what movement the reference star has performed with respect to its previous position. Re-registering is thus not necessary, since the new positional relationship between the reference star and the body or table connected to said reference star can be determined from the positional change in the reference star ascertained by the at least one position detector. Accordingly, the reference star is again in a defined positional relationship to said body or table.

The third transformation can be described by the positional relationship of the body advanced out of the detection range relative to the body within the detection range, wherein the shift by the table on which the body is lying is ascertained. The position of the table or the body after removal then can be detected by a detector, and the table or body can be removed to a known position.

With the aid of the second transformation method, the captured image data defined with respect to a coordinate system whose origin, for example, is formed by the second marker array, can be transformed into another coordinate system whose origin, for example, is formed by the first marker array, arranged in a fixed positional relationship relative to the body. The spatial position of the image data relative to the first marker array is therefore known, such that at any location they are clearly determined with respect to the first marker array. In an operation, for example, the image data can be clearly assigned to a particular point or particular area of the body of a patient.

Providing the body is situated in the detection range, the image data are defined by the first transformation and, therefore, the point of the body at which the respective data have been recorded can be determined. Once the body has been removed from the detection range, the image data regarding the first marker array, which, for example, is or is being attached to the table, can be defined with the aid of the second transformation by ascertaining how far the table or the patient has been removed.

Detecting the image data is not restricted to a particular imaging method but can be performed using any method, such as a computer tomography method, a nuclear spin resonance method, a positron emission tomography (PET) method, a SPECT (single photon emission computed tomography) method, an ultrasound method, or the like.

The method for registering image data also can be configured as a computer program. This computer program, when loaded onto a computer or is running on a computer, can perform the method, in particular automatically, such that it is not necessary for a user to intercede. Thus, for example, the markers could be automatically placed by a control program, the table automatically shifted out of the detection range into a particular position, and/or the transformation or registration method automatically performed. The computer program, for example, can be contained in a program storage medium or computer program product.

A device for registering image data of a body comprises: a camera, preferably formed to be movable, in particular an infrared camera; a first marker array, in particular a marker array that reflects or emits infrared radiation and can be arranged in a fixed positional relationship relative to the body of the patient; and a second marker array, in particular a marker array that reflects or emits infrared radiation and can be arranged at a known fixed position defined with respect to a spatial position (e.g., the detection range). The first marker array can be arranged, preferably fixed or non-movable, in a constant positional relationship or distance relative to the body, for example arranged on the body itself or at a position having a constant distance relative to the body. If the position of the marker arrays relative to each other is known, the position of the first marker array relative to the body shifted out of the detection range is also known due to the known position of the second marker array, in particular due to the known positional relationship of the second marker array relative to the detection range, wherein the position of the second marker array is significant for further navigation.

The device preferably comprises a data capture device for capturing image data of a body, such as a computer tomograph, a nuclear spin or magnetic resonance tomograph or an ultrasound apparatus, wherein the second marker array, for example, is attached to the data capture device and therefore has a known position relative to the detection range and consequently can be used to register the body of the patient following the recording or scanning process.

The device for registering image data of a body preferably comprises a table on which the body of a patient can be situated and which can be moved into and out of the detection range. In particular, the detection range also can be moved along the body, for example by moving the data capture device on rails running parallel to the table or body and fixing and/or moving the table or the body. The first marker array, for example, then can be attached to the table in a fixed positional relationship relative to the body of the patient.

The first marker array thus always can have the same position relative to the body of the patient, which is preferably supported in a fixed or non-movable manner, irrespective of whether the table is situated in the detection range of the data capture apparatus, in an operating theater or at another location. The position of the second marker array relative to the detection range can be ascertained from the first transformation method, determined for example once before recording, or from a registration method performed using a phantom having markers, for example. The position of the body and, therefore, the position of the recorded image data during the recording process relative to the position of the body can be ascertained from the third transformation or registration method. Therefore, the position of the captured image data after the table has been removed from the detection range also can be determined from the third transformation or registration method. With the aid of these positional relationships and the position of the two marker arrays relative to each other, the body, which may have been removed from the detection range, can be registered.

The forgoing and other features of the invention are hereinafter described with reference to the annexed drawings.

DETAILED DESCRIPTION

As was described above, a first transformation is defined as the positional relationship between a second marker array and a detection range, a second transformation is defined as the positional relationship between a first marker array and the second marker array, and the third transformation is defined as a translation, shift or known rotation of a body out of the detection range.

Figure 1:
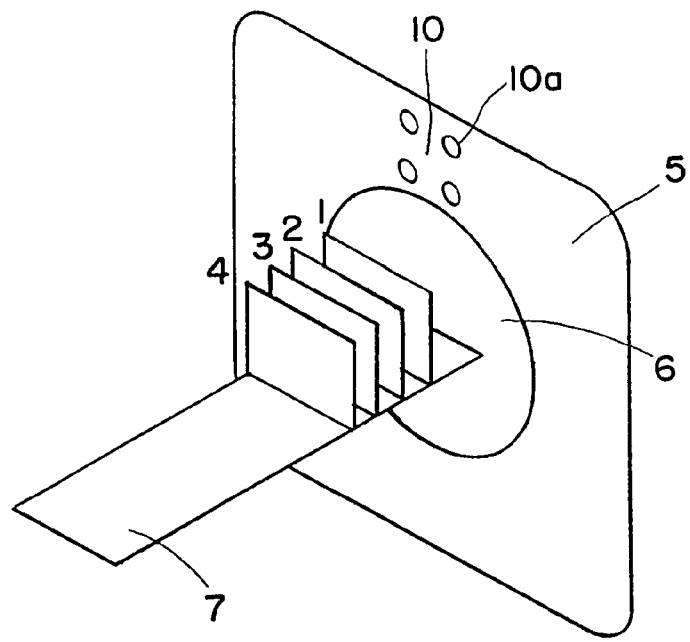
FIG. 1 illustrates an embodiment of a device in accordance with the invention, for capturing image data of a body during a scanning process.

FIG. 1 shows a device for capturing image data of a body, wherein a data capture device 5 is formed as a computer tomograph. A second marker array 10 including four markers 10a is attached to a particular position of the data capture device 5 such that the marker array position does not change during the scanning process and during the subsequent registering process. The body of a patient (not shown) is situated on a movable or non-movable table 7 of the computer tomograph 5, wherein image data captured in a detection range 6 are illustrated by the planes 1 to 4. The image data can be recorded layers of the body, as shown in FIG. 1. These layers or recordings 1 to 4 can be ascertained or detected, as is known from the prior art, wherein the table 7 can be moved during the recording method. For example, the table 7 can be continuously advanced as in spiral computer tomography or in increments, wherein the table 7 is fixed during a recording period and moved through the motionless detection range 6 during a non-recording period. Alternatively, the table 7 may not be moved during the entire recording process and instead, the data capture device 5 together with its detection range 6 can be moved continuously or in increments along the table 7.

Figure 2:
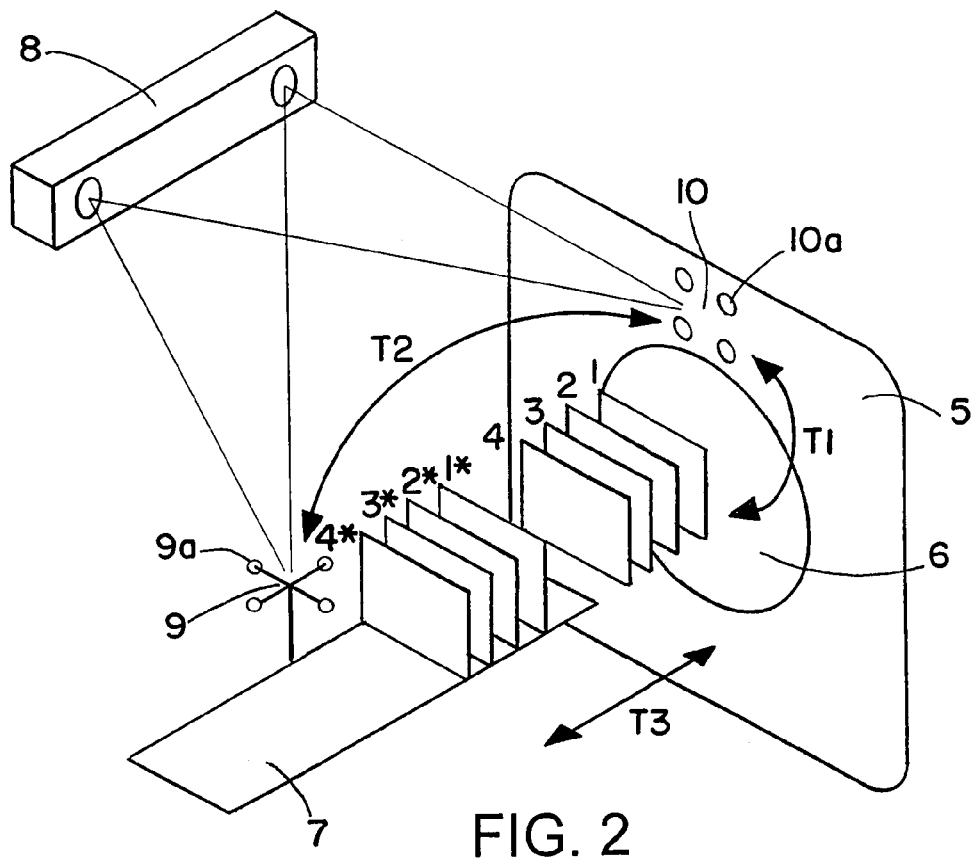
FIG. 2 illustrates an embodiment of a device in accordance with the invention, for registering image data of a body after scanning, during a registering process.

FIG. 2 illustrates the device in accordance with the invention during a registration process, after the table 7 has been scanned and removed. In FIG. 2, the image data in the detection range 6 captured by the scanning process are illustrated by the layers 1 to 4 and the corresponding areas of the removed body 1* to 4*.

In a first transformation or registration method T1, the position of the detection range 6, e.g., the recorded image data, relative to the second marker array 10 attached to the computer tomograph 5 has been determined. Hence, the layers 1 to 4 of the recorded image data can be clearly assigned to the respective points of the recorded body in the detection range 6, provided the patient is situated in the computer tomograph 5. This exact assignment is lost once the patient has been removed from the detection range 6 of the computer tomograph 5.

If, as shown in FIG. 2, another marker array 9 having markers 9a, e.g., in the form of a reference star or including four markers, is then attached to the table 7 and another transformation method T3 is used to describe how far the body of the patient has been removed from the detection range 6, or it is known how far the body of the patient has been removed from the detection range 6, for example to a defined position, then from the first transformation T1 and the third transformation T3, and with knowledge of the positional relationship of the marker arrays relative to each other from the transformation T2, the body can be registered.

In other words, the recording data 1 to 4 can be assigned to the areas of the body 1* to 4* if in the subsequent navigation only the position of the first marker array 9 is detected, e.g., if camera 8 is moved such that the second marker array 10 is no longer visible to the camera. The detected layers 1 to 4 of the body can therefore be assigned such that their position with respect to the first marker array 9 arranged on the table is known. For example, layers 1 to 4 are the data acquired in the detection range, while layers 1* to 4* are the same data but in a different location and fixed to the first marker array 9. Hence, the recorded image data can be clearly assigned to the corresponding point of the body of the patient, irrespective of where the patient is situated and/or where the table 7 has been shifted. Further, since the first marker array 9 is not be attached until after the recording process of the computer tomograph 5, a disruption, for example, by the first marker array 9 attached to the table 7 during the scanning process or while inserting the patient or table 7 into the detection range 6, can be prevented.

Figure 3:
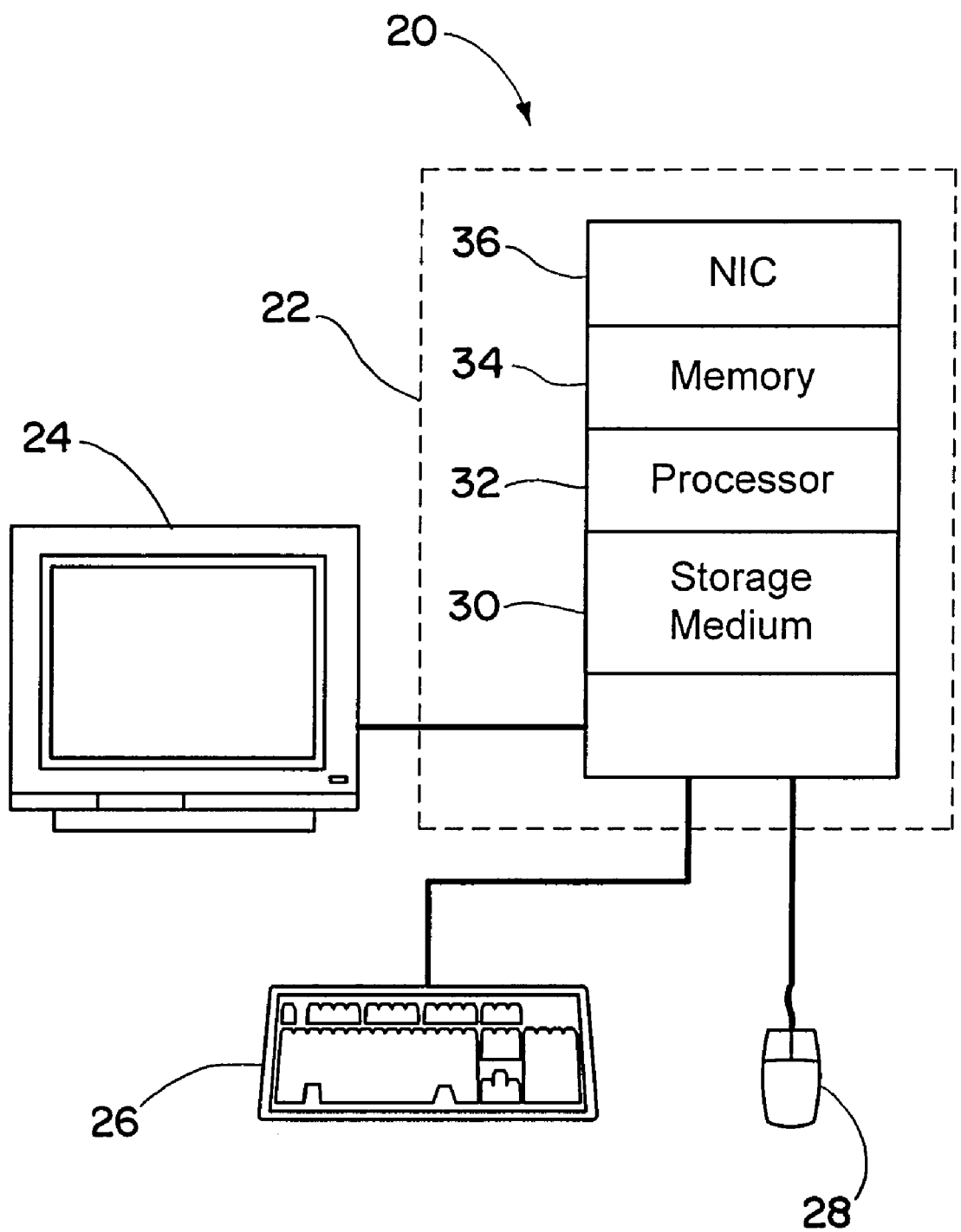
FIG. 3 is a block diagram of a computer system that can be used to implement the method of the present invention.

Moving to FIG. 3, a computer system 20 for executing a computer program in accordance with the present invention is illustrated. The computer system 20 can be communicatively coupled to the cameras 8 to receive positional data therefrom, and to display three-dimensional positional data. The computer system 20 includes a computer 22 for processing data, and a display 24, such as a CRT, LCD, or the like, for viewing system information. A keyboard 26 and pointing device 28 may be used for data entry, data display, screen navigation, etc. The keyboard 26 and pointing device 28 may be separate from the computer 22 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 26 and pointing device 28. A touch screen is well known by those skilled in the art and will not be described in detail herein. Briefly, a touch screen implements a thin transparent membrane over the viewing area of the display 24. Touching the viewing area sends a signal to the computer 22 indicative of the location touched on the screen. The computer 22 may equate the signal in a manner equivalent to a pointing device and act accordingly. For example, an object on the display 24 may be designated in software as having a particular function (e.g., view a different screen). Touching the object may have the same effect as directing the pointing device 28 over the object and selecting the object with the pointing device, e.g., by clicking a mouse. Touch screens may be beneficial when the available space for a keyboard 26 and/or a pointing device 28 is limited.

Included in the computer 22 is a storage medium 30 for storing information, such as application data, screen information, programs, etc. The storage medium 30 may be a hard drive, for example. A processor 32, such as an AMD Athlon 64™ processor or an Intel Pentium IV® processor, combined with a memory 34 and the storage medium 30 execute programs to perform various functions, such as data entry, numerical calculations, screen display, system setup, etc. A network interface card (NIC) 36 allows the computer 22 to communicate with devices external to the computer system 20.

The actual code for performing the functions described herein can be easily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for registering image data of a body, wherein the image data of the body are captured in a detection range of a medical image capture device and the body is subsequently shifted relative to the detection range or vice versa, comprising:
   capturing, via the medical image capture device, image data of the body prior to a first marker array being placed in a fixed positional relationship relative to the body;
   subsequent to capturing the image data, placing the first marker array in a fixed positional relationship relative to the body; and
   registering, with computer assistance, the image data and the body based on a detected position of the first marker array and a second marker array, arranged in a defined positional relationship relative to the detection range.

2. The method as set forth in claim 1, wherein placing the first marker array in a fixed positional relationship relative to the body includes placing the first marker array in a fixed positional relationship relative to the body after the body has been shifted out of the detection range.

3. The method as set forth in claim 1, further comprising performing a first transformation or registration method to define a positional relationship of the second marker array relative to the detection range.

4. The method as set forth in claim 3, further comprising ascertaining data that describes a third transformation, wherein the third transformation describes a positional relationship of the body removed from the detection range relative to the body lying in the detection range.

5. The method as set forth in claim 4, wherein the step of ascertaining data that describes the third transformation includes ascertaining the data from a shift of a table on which the body is lying out of the detection range.

6. The method as set forth in claim 4, further comprising ascertaining data for a second transformation from data of the first and third transformations, the second transformation enabling the image data of the body to be registered.

7. The method as set forth in claim 1, further comprising using a computer tomography method, a nuclear spin resonance method, a positron emission tomography method, a SPECT (single photon emission computed tomography) method or an ultrasound method, to capture the image data of the body.

8. A computer readable medium comprising computer executable instructions adapted to perform the method as set forth in claim 1.

9. A device for registering image data of a body, wherein the image data of the body are captured in a detection range of a medical image capture device and the body is subsequently shifted relative to the detection range or vice versa, comprising:
   a first marker array configured for placement in a fixed positional relationship relative to the body;
   a second marker array placed at a known fixed position relative to the detection range;
   a camera configured to detect a position of the first and second marker arrays; and
   registration logic including
   logic configured to direct the medical image capture device to capture the image data prior to the first marker array being placed in a fixed positional relationship relative to the body, and
   logic configured to register the image data and the body based on the detected position of the first marker array and the second marker array after the first marker array has been placed in a fixed positional relationship relative to the body.

10. The device as set forth in claim 9, further comprising the medical image capture device for capturing the image data.

11. The device as set forth in claim 10, wherein the medical image capture device is a computer tomograph, a nuclear spin tomograph or an ultrasound apparatus.

12. The device as set forth in claim 10, wherein the second marker array is attached to the medical image capture device.

13. The device as set forth in claim 9, wherein the camera is movable.

14. The device as set forth in claim 9, further comprising a table that can be moved into and out of the detection range, or vice versa.

15. The device as set forth in claim 14, wherein the first marker array is configured for attachment to the table.

16. A program embodied in a computer-readable medium for registering image data of a body, wherein the image data of the body are capturable in a detection range of a medical image capture device and after capture the body is shifted relative to the detection range or vice versa, wherein a first marker array is placable in a fixed positional relationship relative to the body and a second marker array is placed in a defined positional relationship relative to the detection range, comprising:
   code configured to capture the image data prior to the first marker array being placed in a fixed positional relationship relative to the body, and
   code configured to register the image data and body based on detected positions of the first marker array and the second marker array after the first marker array has been placed in a fixed positional relationship relative to the body.

17. A system for registering image data of a body, wherein the image data of the body are captured in a detection range of a medical image capture device and the body is subsequently shifted relative to the detection range or vice versa, wherein a first marker array is placable in a fixed positional relationship relative to the body and a second marker array is placed in a defined positional relationship relative to the detection range, comprising:
   a processor circuit having a processor and a memory;
   a registration sub-system stored in the memory and executable by the processor, the registration sub-system comprising:
   logic configured to capture the image data prior to the first marker array being placed in a fixed positional relationship relative to the body, and
   logic configured to register the image data and body based on a detected position of the a first marker array and the second marker array after the first marker array has been placed in a fixed positional relationship relative to the body.

18. The method as set forth in claim 1, wherein the second marker array is positionally fixed relative to the detection range.

* * * * *